Figure 6:
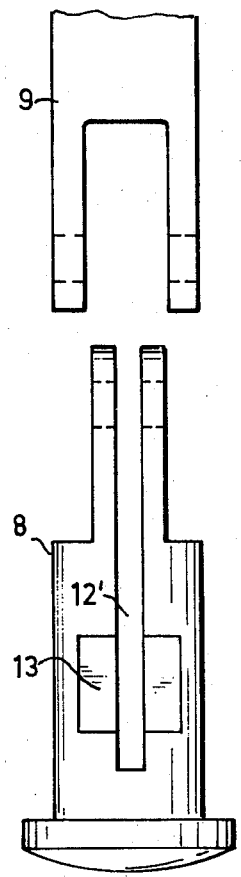

United States Patent [19]

Bjurling et al.

[11] 3,986,743
[45] Oct. 19, 1976

[54] LOCKING TOGGLE JOINT FOR GRIPPING TONGS

[75] Inventors: Per-Olof Bjurling, Gustavsberg; Sven-Eric Juhlin, Ingaro, both of Sweden

[73] Assignee: AB Gustavbergs Fabriker, Gustavsberg, Sweden

[22] Filed: Mar. 18, 1975

[21] Appl. No.: 559,592

[30] Foreign Application Priority Data

Apr. 2, 1974  Sweden.............................. 7404441

[52] U.S. Cl.............................. 294/19 R; 294/100; 403/97
[51] Int. Cl.² .................... B25J 17/00; F16C 11/10
[58] Field of Search................ 294/19 R, 20, 22, 23, 294/24, 53.5, 57, 100, 104, 115; 403/93, 91, 97, 157

[56] References Cited
UNITED STATES PATENTS

| 1,181,137 | 5/1916 | Heggland | 403/97 X |
| 2,392,865 | 1/1946 | Smith | 294/20 |
| 2,680,032 | 6/1954 | McClenahan | 403/97 |
| 3,576,343 | 4/1971 | Juhlin et al. | 294/100 |

Primary Examiner—Evon C. Blunk
Assistant Examiner—Johnny D. Cherry
Attorney, Agent, or Firm—Pierce, Scheffler & Parker

[57] ABSTRACT

The present invention relates to a toggle joint, specially to an angular positioning device for a gripping means for gripping tongs where the movements of the tong jaws of the gripping means are regulated by a control cable whose one end is fixed in the gripping means and whose other end is connected to an operating trigger in the handle of the gripping tongs. Said device is formed as a toggle joint having two cooperating joint surfaces designed with locking means which engage one another and forming clutch couplings.

2 Claims, 6 Drawing Figures

U.S. Patent    Oct. 19, 1976    Sheet 1 of 2    3,986,743
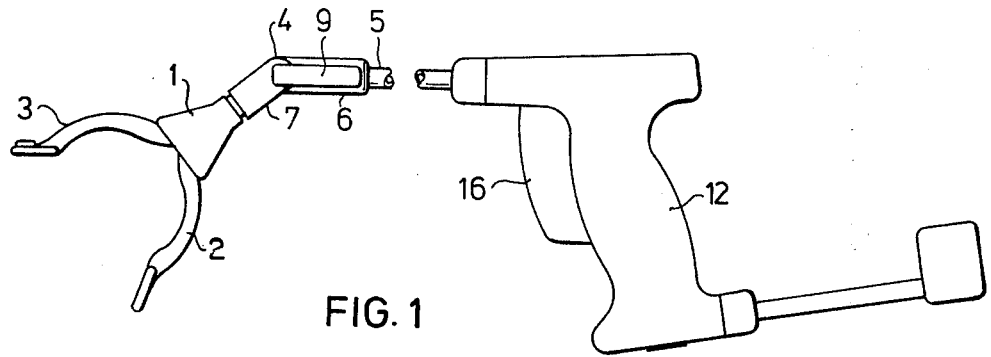
FIG. 1
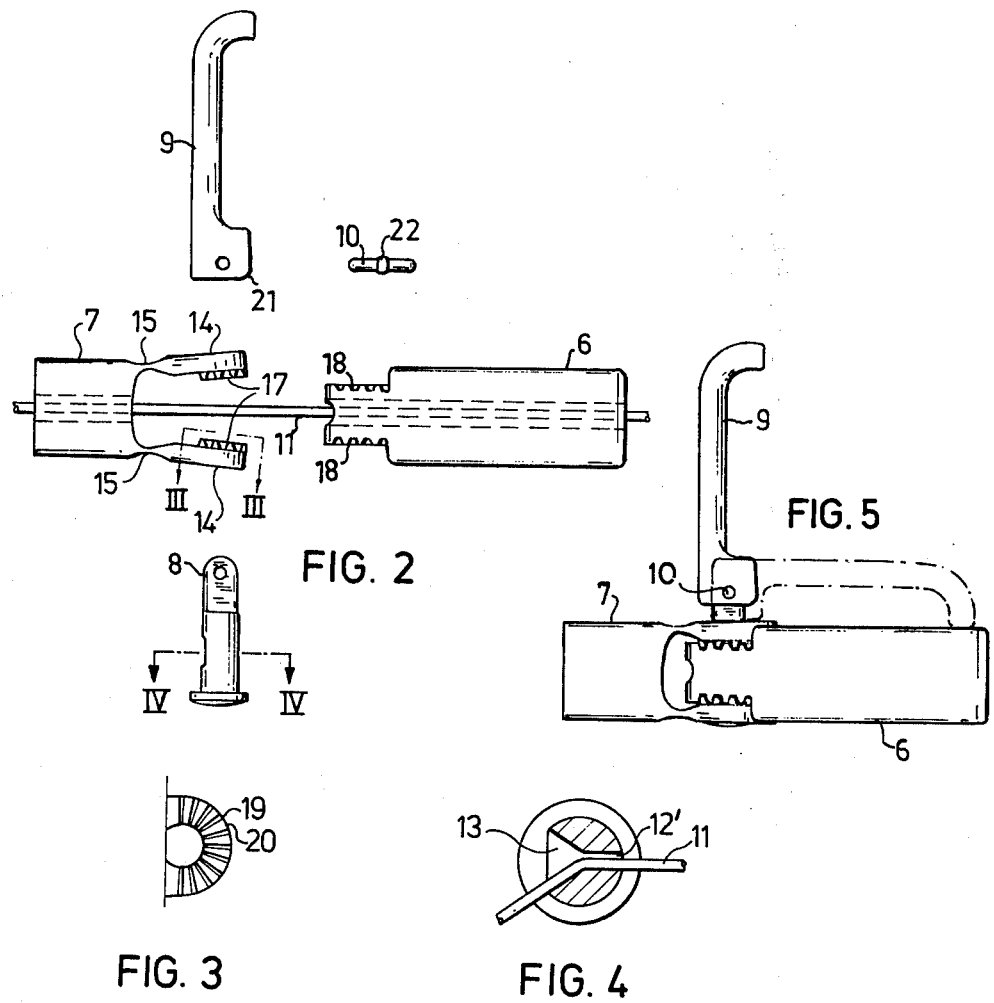
FIG. 2
FIG. 5
FIG. 3
FIG. 4

LOCKING TOGGLE JOINT FOR GRIPPING TONGS

The present invention relates to a toggle joint, preferably for gripping tongs, which by means of a clutch coupling is lockable in various angular positions via an eccentric cam.

Gripping tongs are described in U.S. Pat. No. 3.576.343 which are intended for disabled persons and which are fitted with a joint which can be locked in a selected position. Locking is accomplished solely in that the head of the joint pin presses the contact surface of the one joint member against the contact surface of the second. The required pressure is obtained from an eccentric cam which is journalled in the pointed end of the joint pin and presses the joint members against one another. The strength of the obtained locking is dependent on the friction forces between the surfaces, and when a heavy object is gripped with the tong jaws and is lifted, the ensuing torque in the joint may be so large that it exceeds the friction force between the joint surfaces. In this way the angular adjustment may come out of position, which can mean that the contents of an open vessel which is lifted with the gripping tongs are spilled. A lifting operation of this type is common for individuals confined to wheel chairs when they wish to reach objects on high or low shelves, for example in the kitchen.

In order to avoid the described disadvantages and to assure the locking of the angular position for all weights with which the gripping tongs may be loaded, the following improvement of the joint is proposed.

The inward and outward members of the gripping tongs in the joint which is of the toggle joint type are fitted with double joint surfaces, situated on opposing sides of the joint members and oriented normal to the joint pin. Two pairs of cooperating joint surfaces are thereby obtained which are designed with radial ridges with intermediate grooves to ensure the locking of the joint members relative to one another. The pressing of the joint surfaces against one another takes place by known means, which implies that a lever whose one end is formed as an eccentric cam is employed to effect the compressing force. This has the advantage that it is easy to change the angular position of the gripping means formed by the jaws.

A preferred embodiment of the invention will be described in connection with the attached drawing, in which FIG. 1 shows longitudinally shortened gripping tongs fitted with the toggle joint according to the invention, FIG. 2 shows the details included in the toggle joint separated, but located in proper relation to one another, FIG. 3 shows a projection of a joint surface, seen in the direction of the arrows III—III in FIG. 2, FIG. 4 shows in larger scale a cross section through the joint pin, taken along the line IV—IV in FIG. 2, FIG. 5 shows the details included in the toggle joint assembled, FIG. 6 which shows joint pin 8 turned 90° in relation to FIG. 2.

Gripping tongs are most nearly gripping means 1 designed with tong jaws 2, 3 and furnished with an angular positioning device designed as a toggle joint 4. Said angular positioning device consists of inward joint member 6 affixed to the reach-determining shaft 5 of the gripping tongs and cooperating with outward joint member 7, said members being joined by means of a joint pin 8. Additionally a lever 9 is included which rotates around a pin 10 through the pointed end of the joint pin 8.

The inward joint member 6 has a central, axial through hole through which a control cable 11 passes from the mechanism in the grip tongs handle 12 to the gripping means 1. For the passage of the cable 11 through the joint pin 8, this is formed with an axially running slot 12' which has a widening 13 in the direction of the gripping means 1. The joint pin 8 has been provided with this slot 12', which extends from the pointed end of the pin nearly to its head, in order to facilitate the assembly of the gripping tongs. This namely permits the various members to be threaded onto the control cable 11, which then at its ends is connected to a trigger 16 and to the gripping means 1, respectively, whereafter the joint pin 8 is pressed into the toggle joint 4 from the side. An equivalent assembly procedure would not be possible with a diametric through hole for the passage of the control cable. FIG. 6 shows, in larger scale, slot 12' in joint pin 8, the aforesaid widening 13, and the bifurcated lower end of lever 9 which is fitted to the pointed end of joint pin 8 by pin 10 (see FIG. 5).

The widening 13 of the slot 12' facilitates the movement of the cable 11 through the toggle joint 4 when the gripping means 1 has been angularly positioned via the outward joint member 7.

The outward joint member 7, which is fitted with a central, axial through hole for the passage of the control cable 11, has two lugs 14. These are connected with the joint member 7 by so-called "living hinges", which are obtained by flexible hinges, i.e. making the material, which must have a certain flexibility, somewhat thinner where the lugs 14 join the joint member 7. Because the lugs 14 are designed to diverge somewhat in relation to the shaft 5, a pre-stress in the flexible hinges obtains the function of which will be explained in detail below.

The opposing insides 17 of the lugs 14 have been designed, as have the two joint surfaces 18 on the inward joint member 6, with radially running ridges 19 with intermediate slots 20. In the assembled toggle joint 4 the surfaces formed in this way act as two clutch couplings. The coupling force is obtained from the lever 9, in whose end nearest the center of oscillation an eccentric cam 21 is formed. The lever 9 is affixed at the pointed end of the joint pin 8 by means of the pin 10. This has a center on the same formed thickening 22, which in the assembled gripping tongs is situated in the slot 12' on the joint pin 8, where it is placed permanently by snapping in.

When the gripping means 1 has been placed in the desired angular position the lever 9 is brought from a position normal to the longitudinal axis of the gripping tongs to a position parallel thereto. The eccentric cam 21 then presses against the one lug 14 at the same time as a tension in the joint pin 8 presses its head against the other lug. The insides 17 of the lugs 14 are thereby urged against the joint surfaces 18, whereby the ridges 19 and grooves 20 of the joint surfaces 18 and the insides engage one another. Because the eccentric cam 21 is formed so that its center of pressure has been passed when the lever 9 is moved parallel to the longitudinal axis of the gripping tongs, the lever is locked in this position by friction, and the force holding the clutch couples together is maintained.

When the angular position of the gripping means 1 is to be changed, the lever 9 is turned normal to the longitudinal axis of the gripping tongs. The lugs 14 then spring apart because of the built-in pre-stress in the flexible hinges 15. The locking in the new position then takes place as above.

What we claim is:

1. An angular positioning device for a gripping means for gripping tongs, where the movements of the tong jaws of the gripping means are regulated by a control cable whose one end is fixed in the gripping means and whose other end is connected to an operating trigger in the handle of the gripping tongs, said device being formed as a toggle joint (4) comprising inward and outward joint members (6, 7) having cooperating joint surfaces, the joint surfaces of the outward joint member (7) comprising the insides (17) of a pair of lugs (14) yieldingly connected to the outward member, said cooperating joint surfaces being designed with locking means (19, 20) which engage one another and forming clutch couplings, said inward and outward joint members (6, 7) being held together by a joint pin (8), said pin being axially divided by a slot (12') for receiving the control cable (5), said slot being bevelled to a widening (13) toward the one side of said slot to facilitate the movement of the cable through the toggle joint.

2. The device according to claim 1, wherein the joint members are pressed together by an eccentric cam (21) formed in the one end of a lever (9) pivotally mounted at the joint pin (8).

* * * * *